(12) United States Patent
Manzke et al.

(10) Patent No.: US 9,844,325 B2
(45) Date of Patent: Dec. 19, 2017

(54) VOXEL TAGGING USING FIBER OPTIC SHAPE SENSING (71) Applicant: KONINKLIJKE PHILIPS N.V., Eindhoven (NL)

(72) Inventors: Robert Manzke, Bönebüttel (DE); Bharat Ramachandran, Morganville, NJ (US); Raymond Chan, San Diego, CA (US); Tobias Klinder, Uelzen (DE)

(73) Assignee: Koninklijke Philips N.V., Eindhoven (NL)

( * ) Notice: Subject to any disclaimer, the term of this patent is extended or adjusted under 35 U.S.C. 154(b) by 8 days.

(21) Appl. No.: 14/396,404

(22) PCT Filed: May 14, 2013

(86) PCT No.: PCT/IB2013/053926
§ 371 (c)(1),
(2) Date: Oct. 23, 2014

(87) PCT Pub. No.: WO2013/171672
PCT Pub. Date: Nov. 21, 2013

(65) Prior Publication Data
US 2015/0087927 A1    Mar. 26, 2015

Related U.S. Application Data

(60) Provisional application No. 61/648,641, filed on May 18, 2012.

(51) Int. Cl.
*A61B 5/107*    (2006.01)
*A61B 5/08*    (2006.01)
(Continued)

(52) U.S. Cl.
CPC .......... *A61B 5/1076* (2013.01); *A61B 5/0402* (2013.01); *A61B 5/065* (2013.01);
(Continued)

(58) Field of Classification Search
CPC ..... A61B 5/1076; A61B 5/1079; A61B 5/742; A61B 5/7289; A61B 5/065; A61B 5/0402;
(Continued)

(56) References Cited

U.S. PATENT DOCUMENTS 6,564,088 B1    5/2003    Soller et al.
7,412,573 B2    8/2008    Uratani et al.
(Continued)

FOREIGN PATENT DOCUMENTS

CN    102274006 A    12/2011
EP    1760661 A2    3/2007
(Continued)

*Primary Examiner* — Gary Jackson
*Assistant Examiner* — Scott T Luan (57) ABSTRACT

A voxel tagging system (100) includes a sensing enabled device (104) having an optical fiber (126) configured to sense induced strain within the device (Bragg grating sensor). An interpretation module (112) is configured to receive signals from the optical fiber interacting with an internal organ, e.g. heart, and to interpret the signals to determine positions visited by the at least one optical fiber within the internal organ. A data source (152, 154) is configured to generate data associated with an event or status, e.g. respiration, ECG phase, time stamp, etc. A storage device (116) is configured to store a history (136) of the positions visited in the internal organ and associate the positions with the data generated by the data source (152, 154).

13 Claims, 5 Drawing Sheets

(51) Int. Cl.
*A61B 5/00* (2006.01)
*A61B 5/0402* (2006.01)
*A61B 5/06* (2006.01)
*A61B 5/01* (2006.01)
*A61B 5/145* (2006.01)

(52) U.S. Cl.
CPC .......... *A61B 5/0816* (2013.01); *A61B 5/1079* (2013.01); *A61B 5/7289* (2013.01); *A61B 5/742* (2013.01); *A61B 5/01* (2013.01); *A61B 5/14542* (2013.01); *F04C 2270/041* (2013.01)

(58) Field of Classification Search
CPC ......... A61B 5/14542; A61B 5/01; A61B 5/65; A61B 5/041; A61B 5/0816
See application file for complete search history.

(56) References Cited

U.S. PATENT DOCUMENTS

| | | |
|---|---|---|
| 7,420,555 B1 | 9/2008 | Lee |
| 7,430,309 B2 | 9/2008 | Harel et al. |
| 7,664,221 B2 | 2/2010 | Bruder |
| 2005/0182295 A1* | 8/2005 | Soper .................... A61B 1/0008 600/117 |
| 2008/0285909 A1* | 11/2008 | Younge ................ A61B 5/1076 385/13 |
| 2008/0287803 A1* | 11/2008 | Li ........................... A61B 5/06 600/466 |
| 2009/0137952 A1* | 5/2009 | Ramamurthy ........... A61B 5/06 604/95.01 |
| 2009/0175518 A1 | 7/2009 | Ikuma et al. |
| 2010/0030063 A1 | 2/2010 | Lee et al. |
| 2010/0249507 A1 | 9/2010 | Prisco et al. |
| 2014/0222370 A1 | 8/2014 | Manzke et al. |
| 2015/0087927 A1 | 3/2015 | Manzke et al. |

FOREIGN PATENT DOCUMENTS

| | | |
|---|---|---|
| WO | 2010111090 A1 | 9/2010 |
| WO | 2012049621 A1 | 4/2012 |
| WO | 2013030764 A1 | 3/2013 |

* cited by examiner

VOXEL TAGGING USING FIBER OPTIC SHAPE SENSING

CROSS-REFERENCE TO PRIOR APPLICATIONS

This application is the U.S. National Phase application under 35 U.S.C. §371 of International application Ser. No. PCT/IB2013/053926, filed on May 14, 2013, which claims the benefit of United States Application Serial No. 61/648, 641, filed on May 18, 2012. These applications are hereby incorporated by reference herein.

This disclosure relates to medical instruments and more particularly to shape sensing optical fibers in medical applications for improving curved multi-planar reformation.

In many applications, it is often necessary to understand the features and geometry of internal cavities. This information may not be easily accessible by imaging modalities or may not be easily digitized for use with software programs or analysis tools. In many instances, it is important to know the geometry of an internal cavity or be able to digitally map the internal cavity.

Fiber optic shape sensing and localization delivers accurate, time-resolved reconstructions of medical device shapes, e.g., flexible catheters, during interventional in-body procedures. These device shapes may be employed to better understand the anatomy being analyzed.

In accordance with the present principles, a voxel tagging system includes a sensing enabled device having an optical fiber configured to sense induced strain within the device. An interpretation module is configured to receive signals from the optical fiber interacting with a volume and to interpret the signals to determine positions visited by the at least one optical fiber within the volume. A data source is configured to generate data associated with an event or status. A storage device is configured to store a history of the positions visited in the volume and associate the positions with the data generated by the data source.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods are provided which employ fiber optic shape sens-

2 ing and localization technology to deliver accurate reconstructions of shapes. Accurate shape data may be retrieved by "painting" a structure of interest with a fiber optic shape sensing enabled instrument (e.g., a catheter or the like at the time of an interventional procedure).

In one embodiment, shape data in the form of ultra-dense point clouds can be acquired using fiber optic shape sensing and localization technology. Point-based mesh processing algorithms may be inappropriate given the high data rate of fiber optic shape sensing and localization technology and the complex topology of anatomical structures.

A system is employed which permits mapping of ultra-dense point cloud data into a voxel data set using an index-based look-up mechanism. The voxel data may be processed using, e.g., standard image processing techniques (e.g., de-noising, hole filling, region growing, segmentation, meshing) and/or visualized using volume rendering techniques. The voxel data set can represent a probabilistic map where every voxel indicates a likelihood that the shape sensing enabled device (e.g., a medical device) was present over time and space. The system also permits immediate visualization of shapes and interrogated structures such as chambers or cavities.

Shape sensing based on fiber optics is preferably employed to use inherent backscatter properties of optical fiber. A principle involved makes use of distributed strain measurement in the optical fiber using characteristic Rayleigh backscatter patterns or other reflective features. A fiber optic strain sensing device is mounted on or integrated in a medical instrument or other probing device such that the fiber optic sensing device can map a spatial volume. In one embodiment, space is defined by a reference coordinate system. The space is then occupied by the sensing device, which by its presence senses the open space and its boundaries within the space. This information can be employed to compute the features of the space, the size of the space, etc.

In one illustrative embodiment, a system performs distributed fiber optic sensing to digitally reconstruct a space or volume. The strain measurements are employed to resolve positions along a length of the sensing device to determine specific locations along the sensing device where free space is available to occupy. The sensing device is moved within the space to test the boundaries of the space. As data is collected over time, a three-dimensional volume is defined by accumulated data.

In particularly useful embodiments, systems and methods for temporal imaging of dynamic structures are provided. The temporal information is incorporated from measurements and mapping time-resolved tags into the voxel data set. With appropriate visualization, this allows for display of specific information pertinent to different dynamics, e.g., organ motion behavior. Tagging and visualization of dynamic structure and function is provided through temporal measurements by tagging of the shape data and mapping of this information into the voxel data set. The data set can be displayed having specific morphological and functional information evolving dynamically, e.g. due to organ motion.

Shape data which is acquired using a shape sensing enabled medical device is augmented by time-stamping and application of information tags related to spatially and temporally dependent measurement fields. Such stamps can incorporate information from a global real-time clock and/or information of other monitoring devices such as ECG-data, SpO2, pH, temperature, etc. For example, in the case of ECG measurements, shape sensing information can be tagged with the corresponding cardiac phase during acquisition, e.g., using a shape-sensing-enabled catheter and perform phase resolved painting/mapping to generate point cloud images of the heart at each cardiac phases, analyze its structure and function, and detect abnormalities. Phase-specific data like deformation patterns can easily be processed and visualized when setting the voxel characteristics according to the phase-tag.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Figure 1:
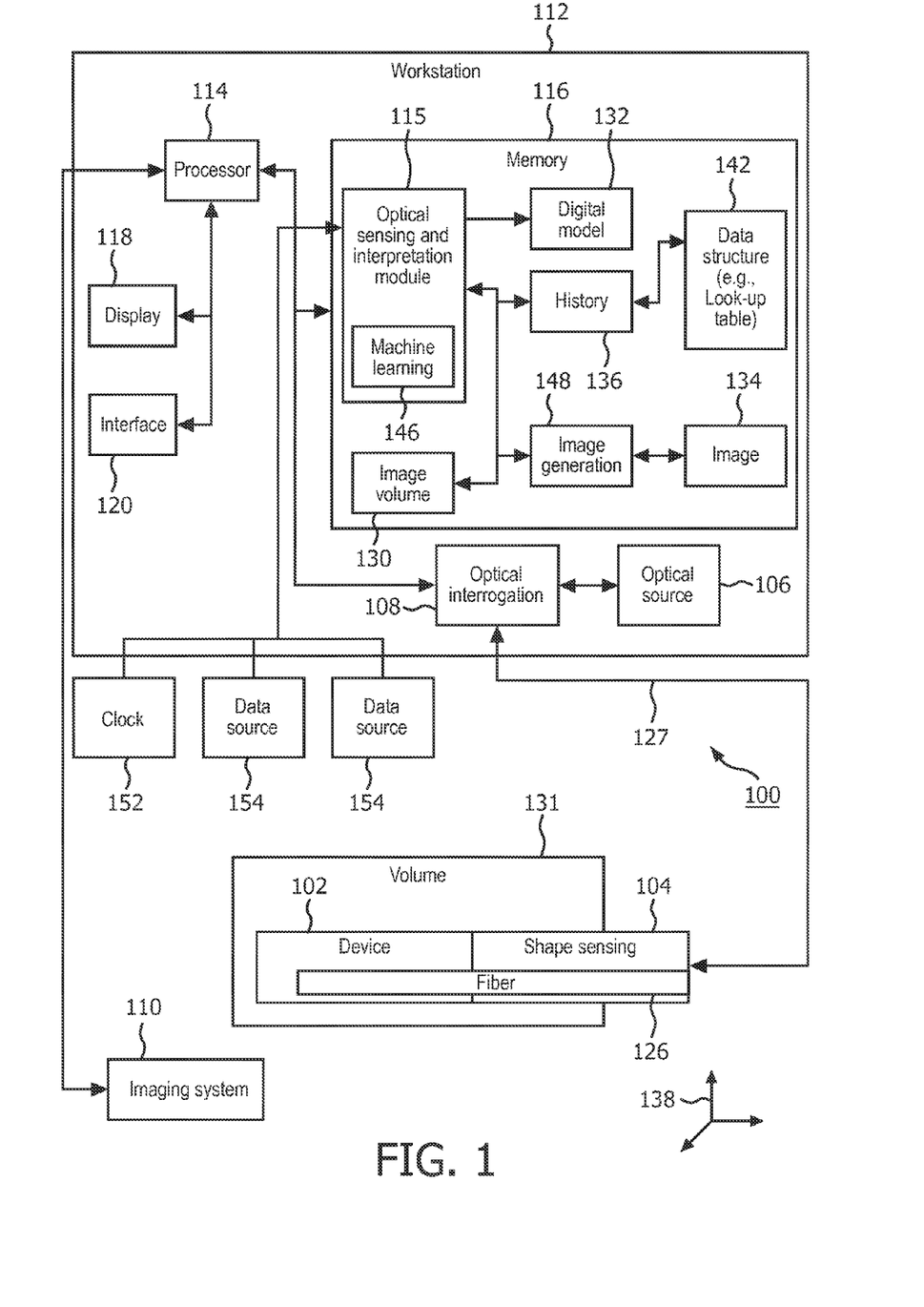
FIG. 1 is a block/flow diagram showing a shape sensing system which tags voxels with monitored event data in accordance with one embodiment.

Referring now to the drawings in which like numerals represent the same or similar elements and initially to FIG. 1, a system 100 for mapping volumes and encoding associated status data is illustratively shown in accordance with one embodiment. System 100 may be employed with, and is applicable for, all applications for interventional and surgical procedures that employ fiber optic shape sensing. In addition, the present principles may be applied to mechanical systems, such as mapping out a cylinder in an engine block, searching a cavity of an antiquity, a space in an architectural setting, etc. Distributed fiber optic sensing of strain may be employed to reconstruct the shape and/or features of a cavity, and/or reconstruct or digitize an interior or exterior surface. By employing the optical fiber over regions of a shape, a data cloud of the shape features can be learned and employed to digitize the shape. In addition, the data in the data cloud is time-stamped and/or encoded with status data provided or measured from a related or unrelated source. As an example, a heart volume may be geometrically mapped using optical fiber sensing. The mapped points may be time stamped and encoded with event data, such as, data relevant to an interventional procedure, such as, blood pressure, SpO2, ECG, etc.

For a medical application, a medical instrument 102 may be equipped with a shape sensing device 104. The shape sensing device 104 on the medical device 102 may be inserted into a volume 131 (e.g., a cavity inside a body). Reflective properties of received light from illuminated optical fibers of the shape sensing device 104 indicate strain measurements which may be interpreted to define a space of the shape sensing device 104. The shape of the shape sensing device 104 is set in a coordinate system 138 to enable the definition of points relative to each other in the space.

System 100 may include a workstation or console 112 from which a procedure is supervised and/or managed. Workstation 112 preferably includes one or more processors 114 and memory 116 for storing programs and applications. Memory 116 may store an optical sensing and interpretation module 115 configured to interpret optical feedback signals from the shape sensing device or system 104. Optical sensing module 115 may be configured to use the optical signal feedback (and any other feedback, e.g., electromagnetic (EM) tracking, etc.) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc. It should be understood that the shape sensing device 104 may be employed with or independently from the medical device 102.

The sensing device 104 connects with an optical interrogator 108 that provides selected signals and receives optical responses. An optical source 106 may be provided as part of the interrogator 108 or as a separate unit for providing light signals to the sensing device 104. Sensing device 104 includes one or more optical fibers 126 which may be coupled to or in the device 102 in a set pattern or patterns. The optical fibers 126 connect to the workstation 112 through cabling 127. The cabling 127 may include fiber optics, electrical connections, other instrumentation, etc., as needed.

Sensing device 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., temperature or strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined and temperature differences can be determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape, temperature and dynamics of the surface of interest can be followed. Other reflective/scatter phenomena may also be employed.

An imaging system 110 may be employed for in-situ imaging of a subject or volume 131 during a procedure. Imaging system 110 may include a fluoroscopy system, a computed tomography (CT) system, an ultrasonic system, etc. The imaging system 110 may be incorporated with the device 102 (e.g., intravenous ultrasound (IVUS), etc.) or may be employed externally to the volume 131. Imaging system 110 may also be employed for collecting and processing pre-operative images (e.g., image volume 130) to map out a region of interest in the subject to create an image volume for registration with shape sensing space. It should be understood that the data from imaging device 110 may be helpful but is not necessary for performing a mapping in accordance with the present principles. Imaging device 110 may provide a reference position as to where a cavity or other region of interest exists within a body but may not provide all the information that is desired or provide a digitized rendition of the space or be capable of resolving all of the internal features of the space.

In one embodiment, workstation 112 includes an image generation module 148 configured to receive feedback from the shape sensing device 104 and record accumulated position data as to where the sensing device 104 has been within the volume 131. An image 134 of a history 136 of the shape sensing device 104 within the space or volume 131 can be displayed on a display device 118. Workstation 112 includes the display 118 for viewing internal images of a subject (patient) or volume 131 and may include the image 134 as an overlay or other rendering of the history 136 of visited positions of the sensing device 104. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In another embodiment, system 100 includes a method or program 136 to compute the history of the shape sensing device 104 within the volume 131 without employing any other imaging or tracking scheme or relying on any outside technology or user observation/intervention. The system 100 computes the points of the shape sensing device 104 dynamically in real-time and knowing coordinate positions of all points along a length of the sensing device 104 within the space 131. The coordinate system 138 is established for the shape sensing device 104 by defining a reference position and then determining distance from that position. This may be done in a number of ways including but not limited to establishing an initial position of the shape sensing device as a reference, employing an image volume 130 and registering the shape sensing space with the image volume 130, etc.

The history 136 of the shape sensing device 104 within the volume 131 may be stored in an index-based voxel coordinate data structure 142, such as a lookup table, which stores information or frequency of visits of the shape sensing device 104. The look-up table 142 includes memory locations or bins associated with positions in the volume 131. Each time the shape sensing enabled device 104 enters a position the look-up table 142 is incremented at that corresponding bin. The binned data may be interpreted or used in many ways. For example, the interpretation module 115 may include a machine learning method 146 or other program or method to identify the volume based upon stored information or history of the shape sensing device 104. The history may be analyzed over time using the interpretation module 115 to compute a deformation of the volume (e.g., due to motion, heartbeats, breathing, etc.) or a derived measure over time (e.g., growth rates, swelling, etc.). The interpretation module 115 may also employ the data to compute a digital model 132 of the volume. This model 132 may be employed for other analysis or study.

The shape sensing device 104 is able to deliver accurate reconstructions of shapes of the space 131. Four-dimensional (3D+time) shapes of, e.g., a 1.5 m tether/fiber can illustratively be reconstructed at a frame rate of, e.g., about 20 Hz providing 30,000 data points every 50 ms, spaced at ~50 micrometer increments along a fiber. This acquisition and reconstruction process results in a data rate of, e.g., about 10 Mbyte/s or roughly 80 Mbit/s which needs to be transferred, for example, over a network or other connection, processed and visualized. Accurate shape data permits a "painting" or mapping of an anatomy of interest (e.g., the walls of space 131). The data rates and memory are illustrative and are system dependent.

It should be understood that for some embodiment, binning of shape sensing data is not necessary to associate event data with the shape sensing results. Shape data which is acquired with the shape sensing device 104 is augmented by time-stamping or by applying measurement tags related to spatiotemporally varying information. Such tags can incorporate information from a clock 152 (e.g., global real-time) and/or measurements from other devices 154. The other devices 154 may include devices such as, e.g., ECG monitor, SpO2 measurement device, pH tester, temperature monitoring device, heart monitors, breathing monitors, etc. The data obtained at a given instance may be stored in a bin or look-up table 142. In other words, a bin or memory location may store geometric data, an associated time stamp, a data reading or status and any other pertinent data.

In the case of ECG data, for example, shape sensing information acquired may be phase-tagged, e.g., from a flexible catheter. The phase tagging may include an encoded value indicating the phase of a heart beat when the shape sensing data was collected. In addition, the data may be time stamped so that continuous temporal data can be collected. Phase resolved 'painting' or mapping of heart structure and function may be performed using the shape sensing data, time stamp and the ECG data. These mapping may include voxels that indicate the shape sensing data, time stamp and the ECG data visually on a display or image. A clinician can then use phase specific point cloud images to diagnose an acute or chronic condition, such as, e.g., looking at images acquired at say, the T-wave to distinguish left ventricular hypertrophy from coronary ischema without injecting a dye or using X-ray imaging. Phase-specific deformation patterns can easily be processed and visualized by using the phase-tag information encoded into the voxel characteristics. Other benefits include reduction of the high number of measurements given from the shape sensing data and conversion into a format that is commonly used in clinical routine (e.g., a DICOM image).

Figure 2:
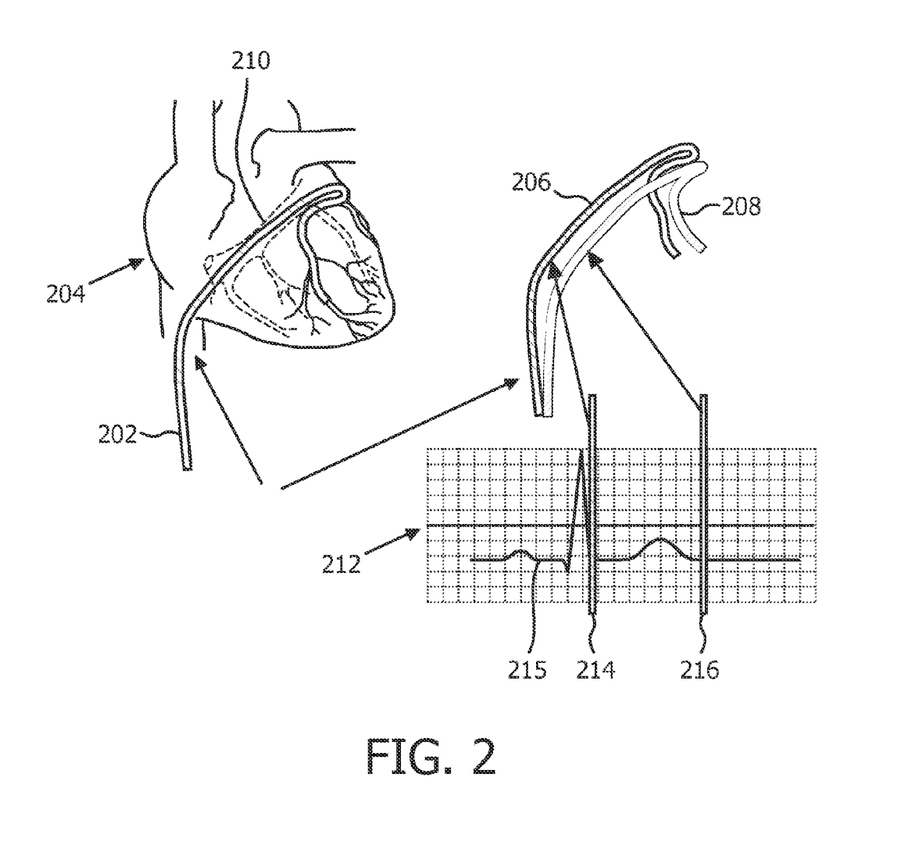
FIG. 2 is a diagram showing coronary anatomy having a shape sensing device disposed therein and showing two shape sensing configurations and an electrocardiogram graph indicating wherein in a heart phase the shape sensing configurations where collected in accordance with one embodiment.

Referring to FIG. 2, a schematic diagram depicts shape sensing enabled device 202 within a coronary anatomy 204. A first shape 206 and a second shape 208 can be 3D visualized and stored using a voxel tagging approach. The first shape 206 and the second shape 208 may be indicated by different colors, textures, symbols, etc. to indicate differences between the shapes 206 and 208. For example, the shapes 206 and 208 indicate different instances or phases of a heartbeat. Any intermediate phases between the first and second shapes 206, 208 can be tagged and visualized as well. A combination of statistics and phase tagging permits a determination of motion patterns and potential pathologies.

In one embodiment, volumetric imaging data are employed for various diagnostic purposes (e.g., vessel dimension and pathology analysis). In accordance with the present principles, the shape sensing device 202, e.g., a catheter equipped with a shape sensing optical fiber, is advanced inside a particular blood vessel 210, say e.g., within a coronary sinus of the heart 204. The shape sensing fiber is contorted in the shape of the blood vessel 210. The shape sensing data provides a real-time snapshot of the blood vessel shape at a plurality of times. The shape of the vessel as provided by the geometry (e.g., three-dimensional shape) over time is captured from the shape sensing device 202 and may be employed to register with image data collected by one or more imaging modalities. The time varying image (206, 208) of voxels for the shapes over time may be employed as a diagnostic tool to determine heart function. An ECG graph 212 shows ECG response 215 and indicates a first position 214 corresponding to a time when the first shape 204 was obtained, and a second position 216 corresponding to a time when the second shape 204 was obtained.

The shape and sensor data (ECG, etc.) may be mapped into a binned voxel data set or map. Alternately, the shape and sensor data may be time stamped, etc. for each shape sensing data frame. Each shape sensing data frame (e.g., first shape 204, second shape 206, etc.) has a corresponding data frame of measurements (e.g., first position 214, second position 216, etc.) from sources such as ECG monitoring data, SpO2 monitoring data, temperature data, respiratory data (e.g., instantaneous inspiratory/expiratory volume, FEV1/FVC ratios (FEV1/FVC ratios are also called Tiffeneau index and are calculated ratios used in the diagnosis of obstructive and restrictive lung disease, etc.), radiation dose data or any other relevant (real-time) medical data.

The information of the corresponding data frame is coded into the voxel locations of the current shape at any given point in time. For example, the voxels may be provided in a geometric shape to indicate the shape sensing data. Each voxel may then include coded information including a time stamp and/or other information. The other information may include direct voxel values that indicate for example, electrical potential, tissue strain or stiffness, a combination of cardiac phase and likelihood of shape (i.e., how often was a voxel 'hit' during multiple cardiac cycles, how long was the shape present, etc. leading to functional information), etc. The other information may be conveyed by voxel characteristics, for example, direct voxel transparency or opacity or color represents respiratory phase or synchronicity relative to other tissue locations or references; voxel shading or reflectivity may be employed to indicate cardiac phase or other data. The spatiotemporal data in the binned voxels can be visualized alongside or together with medical imaging data.

Figure 3:
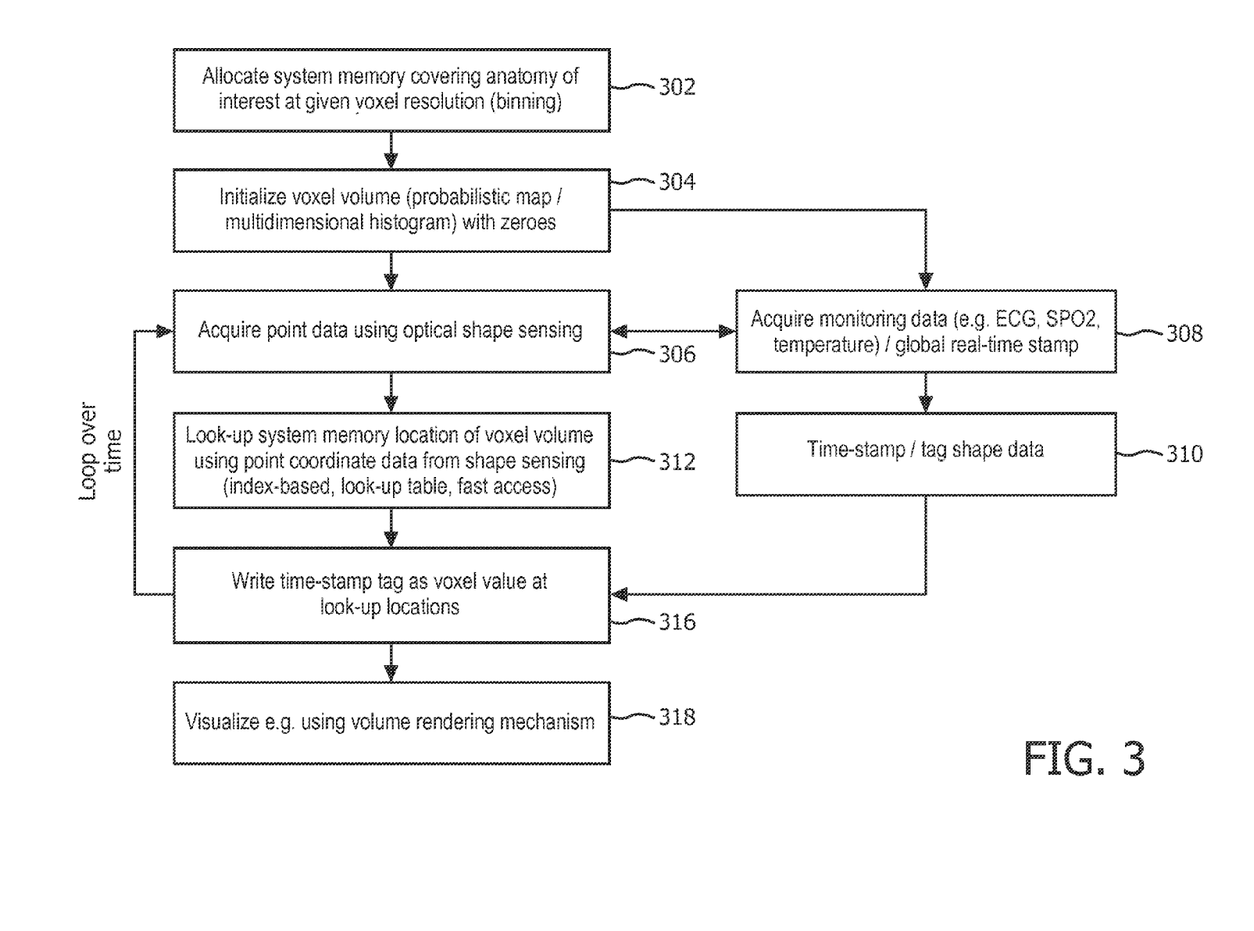
FIG. 3 is a block/flow diagram showing a system/method for tagging voxels using a binning method to mark visited positions in a volume in accordance with one embodiment.

Referring to FIG. 3, a system/method for generating probabilistic maps using fiber optic shape sensing data is illustratively shown. In block 302, system memory is allocated. Given a shape sensing enabled device such as a catheter, a user needs to define a location and dimensions of a field-of-view (FOV). In case of a 1.5 m fiber, the FOV can be set to a maximum of, e.g., 3×3×3 $m^3$. Given the accuracy of the shape sensing system of about 1 mm at 1 m fiber length, one may want to set the voxel dimensions for volume binning to say 2 mm. This would result in a volume size of $(1500)^3$ voxels needing about 13 Gbytes memory (using a 4 byte data type). In practice, however, the anatomy of interest is most probably a much smaller volume, say about 300 $mm^3$ resulting in about 13 Mbytes memory requirements. Once the system memory is allocated, the memory (e.g., space for a probabilistic map or multidimensional histogram) is initialized with zeroes at each bin location in block 304. The voxel volume pixels will represent a probabilistic map or multi-dimensional histogram of visited space.

In block 306, the shape sensing device is introduced to a volume to be mapped. Point data is acquired using all or part of the shape sensing device. The shape sensing device may be articulated in the volume to cover the entire volume with the shape sensing device to simply collect shape sensing data for a given configuration. In some embodiments, the boundaries of the volume should be swept with a higher frequency to assist in defining the entire volume or objects/features contained therein.

In block 308, monitoring data, status data, timestamps, etc. are provided or collected. The monitoring data may include data from one or more devices. The monitoring data may include data relevant to a particular operation or event, and is preferably useful for further diagnosis or understanding. Non-relevant or partially relevant data may also be collected (e.g., a clinician's name, etc.). As described above, the monitoring data may include ECG data, $SpO_2$ data, pH data, temperature, breathing cycle, heart phase, etc.

In block 310, the time stamping or tagging of shape sensing data is performed. This includes correlating the acquired point data with the monitored or event data. In this way, a voxel is defined by three-dimensional position (and time) is tagged with or associated with the timestamp and/or monitored data. In block 312, in a binning approach for gathering statistical or frequency of visits data, a system memory location is looked up in a voxel volume by using an index or coordinate system for shape sensing data frames. The voxel volume if traversed by one or more methods including, e.g., an index-based method, a look-up table, a fast access method, etc. The shape data may be mapped into the volume using an index-based voxel coordinate lookup, e.g.:

$$x_{voxel,i} = \left[\frac{x_{fiber,i} - x_0}{d_x}\right],$$

$$y_{voxel,i} = \left[\frac{y_{fiber,i} - y_0}{dy}\right],$$

$$z_{voxel,i} = \left[\frac{z_{fiber,i} - z_0}{dz}\right],$$

$$index_i = x_{voxel,i} + y_{voxel,i} * sx + z_{voxel,i} * sx * sy$$

where $x_{voxel,i}$ corresponds to the index of the voxel x-coordinate interrogated with the fiber optic shape sensing device along fiber index position i ($x_{fiber,i}$), $x_0$ is the x-offset of the voxel volume given the coordinate system origin of the shape sensing device and dx is the voxel resolution along the x-axis in mm. $index_i$ is the index look-up position within the voxel data set given a linear data array at fiber index position i. The same holds for each of the y and z directions. sx is the voxel grid size along the x-dimension (for sy along the y-direction). If the index is negative or larger than the array size, the shape sensing measurement is outside the FOV. Other indexing schemes may also be employed.

In one embodiment, once the index position within the voxel volume is calculated, the voxel value is incremented by one (or set to any other desired value/modification by any other operation) when the shape sensing device is determined to be in the corresponding indexed position thereby creating a probabilistic map. This indicates where the shape sensing device was physically present in space and for how much time. In block 316, the position may be associated with look-up table of positions. The look-up table may store the position, time (timestamp) and the monitoring data. In addition, a cumulative number of visits to a particular location may also be stored. The time stamp tag or other monitored data may be written into a corresponding voxel location.

The process may be looped over time, returning to block 306 for new positions or times of the shape sensing device. Note that the voxel access has to be repeated for each measurement point along the fiber at the acquisition frame rate, e.g., 20 Hz (e.g., downsampling fiber element size to say about 1 mm can dramatically increase speed).

In block 318, a resulting voxel map with encoded timestamps and/or with monitored data may be output or displayed. In some embodiments, the voxel map can be visualized using volume rendering, multiplanar reformatting (MPR), maximum intensity projection (MIP), or surface rendering (e.g., isosurface visualization) methods to name a few illustrative methods. If a binning method is employed, the voxelized shape sensed data permits rendering of the most likely areas where the device was present. This could be, for example, a heart chamber. The shape of the heart chamber would be hyperintense in the volume rendering for most dominant cardiac and breathing phases. The voxelized shape sensed data may be encoded with timestamps and/or monitored data.

A further embodiment includes functional imaging while interrogating for extended time periods (e.g., hyperintense regions with little movement have a higher likelihood that the shape sensing device is present, and hypointense fast moving regions have less likelihood that the device is/was present). In this way, mechanical dyssynchrony can be estimated comparing the intensity of the point cloud voxel images along different regions of say the left ventricle. Cardiac output can be estimated by comparing hypointense regions corresponding to the region of moving myocardium and the hyperintense regions corresponding to the main body of the cavity. Other applications are also contemplated.

Voxelized point cloud images can be coupled with machine learning algorithms or other data processing algorithms to automate identification of anatomical targets of interest, delineate target regions, modify imaging system or interventional system settings to optimize diagnostic or therapeutic efficacy.

Figure 4:
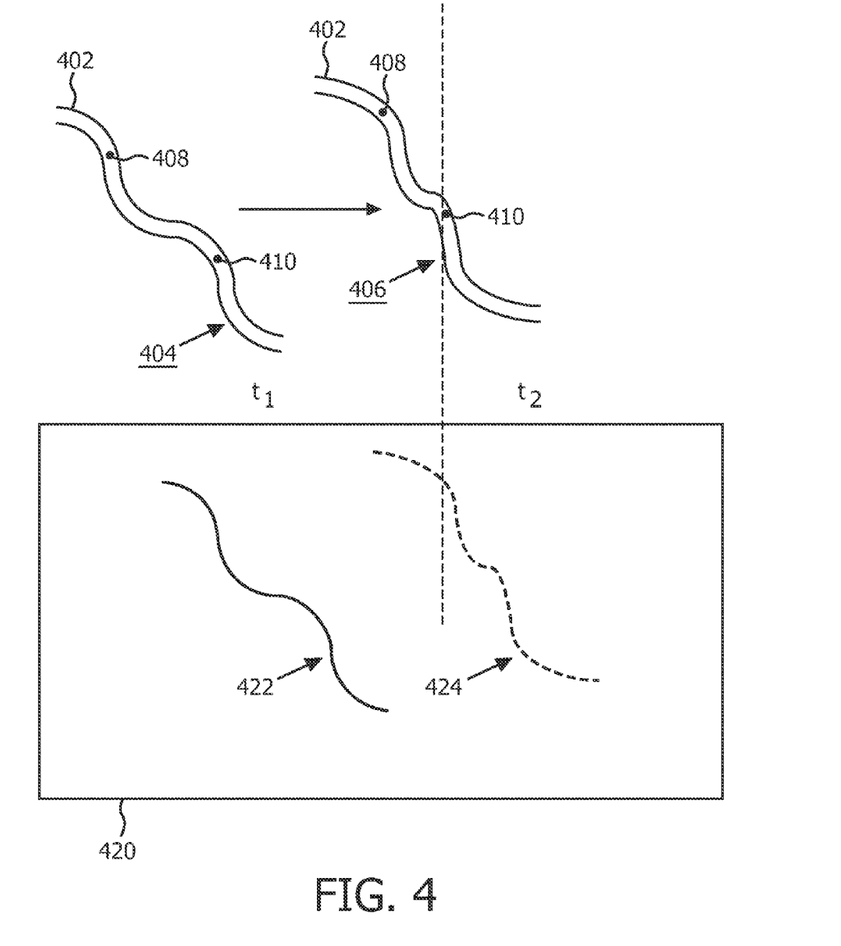
FIG. 4 is a diagram showing two shape sensing configurations and a resultant display showing distinctions based up event data and/or timestamps in accordance with the present principles.

Referring to FIG. 4, an example of a shape sensing device 402 in two configurations 404 and 406 is shown at two separate times $t_1$ and $t_2$, respectively. Each configuration 404 and 406 includes two nodes 408 and 410 (for simplicity) having coordinates $x_1$, $y_1$, $z_1$ and $x_2$, $y_2$, $z_2$ (in configuration 404) and $x'_1$, $y'_1$, $z'_1$ and $x'_2$, $y'_2$, $z'_2$ (in configuration 406), respectively. At $t_1$, a sensor provides a monitored data value of $V_1$ (e.g., a potential, temperature, etc.). At $t_2$, a sensor provides a monitored data value of $V_2$ (e.g., a potential, temperature, etc.).

Table I shows a lookup table having shape sensing position data correlated with a timestamp and/or monitored data values.

TABLE 1

| x-Position | y-Position | z-Position | Timestamp | Monitored Data |
|---|---|---|---|---|
| $x_1$ | $y_1$ | $z_1$ | $t_1$ | $V_1$ |
| $x_2$ | $y_2$ | $z_2$ | $t_1$ | $V_1$ |
| $x'_1$ | $y'_1$ | $z'_1$ | $t_2$ | $V_2$ |
| $x'_2$ | $y'_2$ | $z'_2$ | $t_2$ | $V_2$ |

Voxelized shape sensing data combined with other sensor data may be displayed or otherwise employed to identify and associate volume motion (e.g., heart chamber motion) with other parameters, such as time or sensor data. Using the shape sensing data over time, an estimate of the shape/motion of the volume can be estimated. In FIG. 4, a display panel 420 is illustratively depicted showing the two configurations 404 and 406 at separate times. Voxels of positions of the two configurations 404 and 406 in images 422 and 424 show different textures (in this case, a bold solid line versus a dashed line) to indicate different times ($t_1$ versus $t_2$) or different magnitudes of monitored data ($V_1$ versus $V_2$). It should be understood that other textures, colors, symbols, etc. may be employed to indicate differences in acquired data displays.

Voxel-based image processing may be performed on the data set. This may include modifying color-maps, opacity/translucency look up tables, etc. The voxel data set can be processed using image processing techniques (e.g., de-noising, hole filling, region growing, segmentation, meshing) and/or visualized using volume rendering techniques. In another embodiment, encoding of other information such as electrical potentials measured at corresponding fiber optic shape sensing node locations may be considered. Such data can be encoded in the voxel data set, using, for example, Red Green Blue Alpha (RGBA) or other date types for volume rendering. The voxel-based data set may be employed to compute a mesh or other computational model, which may be employed to perform finite element analysis or other analysis.

Figure 5:
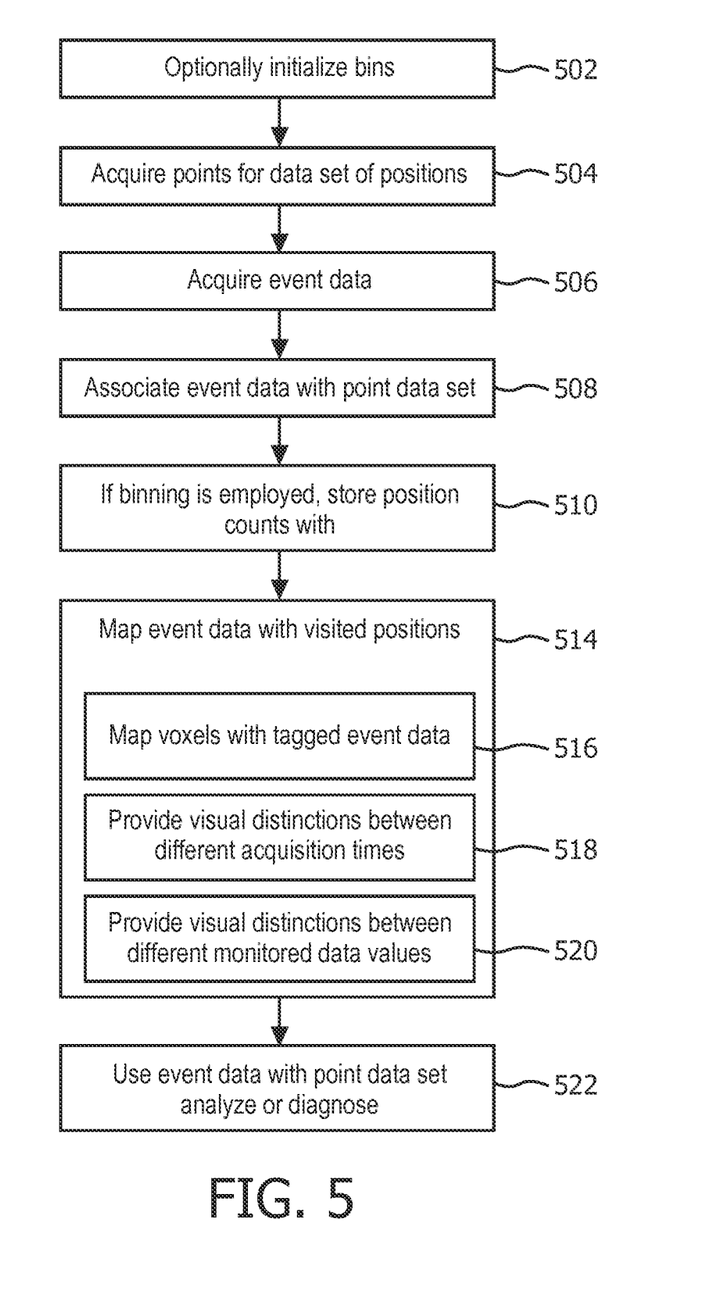
FIG. 5 is a block/flow diagram showing a system/method for associating shape data with event data in accordance with another embodiment.

Referring to FIG. 5, a method for mapping a volume using event data is illustratively shown in accordance with the present principles. In block 502, memory locations corresponding to positions in a volume may optionally be initialized to set up bins. The bins are useful if the volume is to be mapped out using shape sensing data. It should be understood that the present principles may be practiced without the use of bins. In block 504, a data set of visited positions in the volume is acquired by exploring the volume with a fiber optic shape sensing enabled device. The shape sensing enabled device may be included in a medical device and the volume may include an internal cavity in a body.

In block 506, event data from at least one data source is acquired. The at least one data source may include a monitoring device that monitors one or more health parameters. The data structure may store health parameter data associated with the visited positions in the volume. The at least one data source may include an electrocardiogram (ECG) device that monitors heart phase, and the data structure may store the heart phase associated with the visited positions in the volume. The at least one data source may include a respiratory device that monitors breathing, and the data structure may store breathing cycle information associated with the visited positions in the volume. The at least one data source may include a clock, and the data structure may store a timestamp associated with the visited positions in the volume. Other data sources, devices, sensors, etc. may also be employed to provide event data.

In block 508, the event data is associated with the data set of visited positions by recording the event data with the visited positions in a data structure. In block 510, the visited position counts are stored in indexed bins corresponding to positions in the volume.

In block 514, the event data is mapped with the data set of visited positions. The mapping may include generating a voxel map showing the shape sensing data with the event data in block 516. In block 518, generating the voxel map may include providing visual distinctions indicating different acquisition times. In block 520, generating the voxel map may include providing visual distinctions indicating different values for monitored data. The visual distinctions may include colors, textures, patterns, opacity, symbols, etc. In block 522, the information in the data structure may be employed to analyze or diagnose physical phenomena occurring in a patient.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for voxel tagging using fiber optic shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

The invention claimed is:

1. A system, comprising:
 at least one processor;
 memory;
 a device having at least one optical fiber configured to sense induced strain within the device;
 an interpretation module configured to receive signals from the at least one optical fiber interacting with a volume and to interpret the signals to determine positions visited by the at least one optical fiber within the volume;
 a data source comprising a monitoring device that monitors one or more health parameters, wherein the data source generates data including health parameter data associated with an event or status, wherein the data is not derived from sensing by the at least one optical fiber; and
 a storage device that stores a history of the positions visited in the volume and the data including health parameter data generated by the data source and associates the positions with the data including health parameter data generated by the data source.

2. The system as recited in claim 1, wherein the data source includes a clock and the storage device stores timestamps associated with the positions in the volume.

3. The system as recited in claim 1, wherein the device having at least one optical fiber is included in a medical device and the volume includes an internal cavity in a body.

4. The system as recited in claim 1, wherein the monitoring device includes at least one of (i) an electrocardiogram device that monitors heart phase or (ii) a respiratory device that monitors breathing, and the storage device stores at least one of (i) the heart phase associated with the positions in the volume or (ii) breathing cycle information associated with the positions in the volume.

5. The system as recited in claim 1, further comprising a display configured to display voxel maps corresponding to the history.

6. The system as recited in claim 5, wherein the voxel maps include visual distinctions indicating at least one of (i) different acquisition times or (ii) different values for monitored data.

7. A system, comprising:
 a device having at least one optical fiber configured to sense induced strain in the device;
 a data source comprising a monitoring device that monitors one or more health parameters, wherein the data source generates event data including health parameter data associated with an event or status and the event data is not derived from sensing by the at least one optical fiber;
 a processor;
 a memory that stores an index-based voxel coordinate lookup table where indexed bins, corresponding to positions in a volume to be mapped, store the event data to provide a history of a number of visits to corresponding positions by the at least one optical fiber and the event data associated with the positions in the volume;

an interpretation module stored in the memory, said interpretation module being configured to receive signals from the at least one optical fiber interacting with the volume and to interpret the signals to determine visited positions by the at least one optical fiber within the volume; and a display that renders a map of the visited positions in the volume and indicates the event data associated with the positions.

8. The system as recited in claim 7, wherein the data source includes a clock and the storage device stores timestamps associated with the positions in the volume.

9. The system as recited in claim 7, wherein the device having at least one optical fiber is included in a medical device and the volume includes an internal cavity in a body.

10. The system as recited in claim 9, wherein the monitoring device includes at least one of (i) an electrocardiogram device that monitors heart phase or (ii) a respiratory device that monitors breathing, and the storage device stores at least one of (i) the heart phase associated with the positions in the volume or (ii) breathing cycle information associated with the positions in the volume.

11. The system as recited in claim 9, wherein the map includes a voxel map showing the history.

12. The system as recited in claim 11, wherein the voxel map includes visual distinctions indicating at least one of (i) different acquisition times or (ii) different values for monitored data.

13. A method for mapping a volume, comprising:

acquiring a data set of visited positions in the volume by exploring the volume with a fiber optic shape sensing enabled device;

acquiring event data from at least one data source comprising a monitoring device that monitors one or more health parameters, wherein the event data includes health para data and is not derived from sensing by the fiber optic shape sensing enabled device;

associating the event data with the data set of visited positions by recording the event data with the visited positions in a data structure; and mapping the event data with the data set of visited positions.

* * * * *